(12) United States Patent
Oda

(10) Patent No.: US 10,018,989 B2
(45) Date of Patent: Jul. 10, 2018

(54) METHOD OF EVALUATING A MACHINED SURFACE OF A WORKPIECE, A CONTROLLING APPARATUS AND A MACHINE TOOL

(71) Applicant: MAKINO MILLING MACHINE CO., LTD., Tokyo (JP)

(72) Inventor: Mitsunari Oda, Aiko-gun (JP)

(73) Assignee: MAKINO MILLING MACHINE CO., LTD., Tokyo (JP)

( * ) Notice: Subject to any disclaimer, the term of this patent is extended or adjusted under 35 U.S.C. 154(b) by 361 days.

(21) Appl. No.: 14/780,943

(22) PCT Filed: Mar. 29, 2013

(86) PCT No.: PCT/JP2013/059729
§ 371 (c)(1),
(2) Date: Sep. 28, 2015

(87) PCT Pub. No.: WO2014/155727
PCT Pub. Date: Oct. 2, 2014

(65) Prior Publication Data
US 2016/0054724 A1 Feb. 25, 2016

(51) Int. Cl.
*G06F 19/00* (2018.01)
*G05B 19/4069* (2006.01)
(Continued)

(52) U.S. Cl.
CPC .......... *G05B 19/4069* (2013.01); *G01B 11/30* (2013.01); *G01B 17/08* (2013.01);
(Continued)

(58) Field of Classification Search
CPC .. G01N 21/57; G01N 21/55; G01N 2021/557; G05B 19/4069;
(Continued)

(56) References Cited

U.S. PATENT DOCUMENTS 4,365,873 A * 12/1982 Ginsburg ................. A61B 3/06
351/239
5,075,204 A * 12/1991 Shiba ................... G03C 7/3003
430/496
(Continued)

FOREIGN PATENT DOCUMENTS

CN 102227696 10/2011
EP 1 296 210 3/2003
(Continued)

OTHER PUBLICATIONS

Fagiani et al. (Tactile perception by friction induced vibrations, Tribology International 44 (2011) 1100-1110.*
(Continued)

*Primary Examiner* — Darrin Dunn
(74) *Attorney, Agent, or Firm* — Morrison & Foerster LLP

(57) ABSTRACT

A worked surface of a workpiece is evaluated on the basis of how the surface is actually perceived by a person's (observer's) eyes (vision) or fingers (touch), and a work process whereby a workpiece is worked is changed on the basis of the evaluation.

1 Claim, 10 Drawing Sheets

(51) Int. Cl.
*G05B 19/4093* (2006.01)
*G01N 21/47* (2006.01)
*G01B 11/30* (2006.01)
*G01B 17/08* (2006.01)

(52) U.S. Cl.
CPC ..... *G01N 21/4738* (2013.01); *G05B 19/4093* (2013.01); *G05B 2219/32177* (2013.01); *G05B 2219/32215* (2013.01); *G05B 2219/32216* (2013.01); *G05B 2219/35346* (2013.01); *G05B 2219/37402* (2013.01); *Y02P 90/22* (2015.11); *Y02P 90/265* (2015.11)

(58) Field of Classification Search
CPC ...... G05B 2219/35318; G05B 19/4183; G05B 2219/32177; G01B 11/30; G01B 17/08; A61B 3/022; A61B 3/06
See application file for complete search history.

(56) References Cited

U.S. PATENT DOCUMENTS

| | | | | |
|---|---|---|---|---|
| 5,155,558 | A * | 10/1992 | Tannenbaum | G01N 21/57 348/128 |
| 5,710,709 | A | 1/1998 | Oliver et al. | |
| 5,897,184 | A * | 4/1999 | Eichenlaub | G02B 6/0031 348/E13.029 |
| 6,320,272 | B1 * | 11/2001 | Lading | F03D 7/0224 290/44 |
| 6,341,996 | B1 * | 1/2002 | Brien | G05B 19/4069 451/10 |
| 6,435,014 | B1 | 8/2002 | Palmquist et al. | |
| 8,570,291 | B2 | 10/2013 | Motomura et al. | |
| 8,620,033 | B2 * | 12/2013 | Bitzel, Jr. | G01B 11/303 382/108 |
| 8,867,043 | B2 * | 10/2014 | Schwarz | G01B 11/0608 356/406 |
| 2003/0023336 | A1 * | 1/2003 | Kreidler | G05B 19/4183 700/108 |
| 2004/0107077 | A1 * | 6/2004 | Sinha | G06Q 30/02 703/2 |
| 2005/0253510 | A1 * | 11/2005 | Nasu | H05B 33/22 313/509 |
| 2006/0169051 | A1 * | 8/2006 | Alman | G01B 11/303 73/762 |
| 2007/0026679 | A1 * | 2/2007 | Yu | G02F 1/133553 438/690 |
| 2010/0023084 | A1 * | 1/2010 | Gunderson | A61N 1/3706 607/28 |
| 2011/0080412 | A1 * | 4/2011 | Miyata | G05B 19/4069 345/473 |
| 2013/0121018 | A1 * | 5/2013 | Sasaki | G02B 5/02 362/602 |
| 2013/0173046 | A1 * | 7/2013 | Kawana | G05B 19/404 700/186 |
| 2013/0252271 | A1 * | 9/2013 | Ullery | C12Q 1/04 435/29 |
| 2013/0307789 | A1 * | 11/2013 | Karamath | G06F 3/016 345/173 |
| 2014/0117667 | A1 * | 5/2014 | Holstein | F03B 11/04 290/43 |
| 2014/0193254 | A1 * | 7/2014 | Gopolan | F03D 7/022 416/1 |
| 2014/0241878 | A1 * | 8/2014 | Herrig | F03D 7/0224 416/1 |
| 2015/0158148 | A1 * | 6/2015 | Sharmila | B24D 11/02 451/527 |
| 2016/0054724 | A1 * | 2/2016 | Oda | G05B 19/4093 700/109 |
| 2016/0147213 | A1 * | 5/2016 | Murakami | G05B 19/19 700/188 |
| 2016/0243866 | A1 * | 8/2016 | Yokozawa | G03G 15/5029 |
| 2017/0004385 | A1 * | 1/2017 | Aoba | G06K 9/00208 |
| 2017/0216990 | A1 * | 8/2017 | Messmer | B24B 29/00 |

FOREIGN PATENT DOCUMENTS

| | | |
|---|---|---|
| JP | 6-201307 | 7/1994 |
| JP | 8-297024 | 11/1996 |
| JP | 9-47939 | 2/1997 |
| JP | 9-90867 | 4/1997 |
| JP | 2003-5811 | 1/2003 |
| JP | 2003-500677 | 1/2003 |
| JP | 2007-219957 | 8/2007 |
| JP | 2011-185659 | 9/2011 |
| JP | 2012-84079 | 4/2012 |
| JP | 2012-206195 | 10/2012 |
| JP | 2012-215486 | 11/2012 |
| WO | WO-2010/134349 | 11/2010 |
| WO | WO-2011/027535 | 3/2011 |

OTHER PUBLICATIONS

Ho et al., How surface roughness of illumination affects visually perceived surface roughness, journal of vision, 2006, 6, 634-648.*
International Search Report dated Jul. 9, 2013, directed to International Application No. PCT/JP2013/059729, 2 pages.

* cited by examiner

METHOD OF EVALUATING A MACHINED SURFACE OF A WORKPIECE, A CONTROLLING APPARATUS AND A MACHINE TOOL

CROSS-REFERENCE TO RELATED APPLICATIONS

This application is a U.S. National Phase patent application of International Patent Application No. PCT/JP2013/059729, filed on Mar. 29, 2013, which is hereby incorporated by reference in the present disclosure in its entirety.

FIELD OF THE INVENTION

The invention relates to a method of evaluating a surface of a workpiece processed by a machine tool, a controlling apparatus a machine tool using the evaluating method and a machine tool with the controlling apparatus.

BACKGROUND OF THE INVENTION

In the case of a workpiece processed by a machine tool, generally, the criteria for evaluating the machined surface is surface accuracy, in particular surface roughness of the machined surfaces of the workpiece. Conventionally, the lower the surface roughness, the more it is regarded as good machining. However, recently, due to strips, caused by cusps formed on the machined surfaces, observed during a visual inspection by an observer or gritty-texture sensed by an observer when he touched the surfaces with his finger, there are times when the processed workpiece is rejected, even if the surface roughness of the processed workpiece is lower than acceptable by a user. For this reason, technologies have been proposed to measure the shiny appearance or the texture of a machined surface in addition to the simple measurement of the surface roughness. In this context, it should be noted that cusp means unprocessed micro portions on the machined surfaces of the workpiece or micro protrusions and concaves formed in the machined surfaces by vibrations of the machine tool induced by servo-control when a workpiece is cut with a rotating tool along a tool path including pick feeds or scraped with a spring-necked bit.

Patent Literature 1, for example, describes a method for evaluating surface property, relative to criteria of a plurality of measuring items, including specularity, by projecting a cross-stripes pattern, displayed on a display, to a surface to be measured, capturing the reflected image by an image pick up, and measuring the image data by a computer relative to specularity, the dispersion of the specularity, glossiness, sharpness, undulation or form error, contrast and opacity sequentially. Further, Patent Literature 1 describes, as a prior art, a method for measuring surface property by using a specular gloss meter for measuring the glossiness based on the amount of light received.

Further, Patent Literature 2 describes a method for measuring surface texture by combining maximum height of a shape (Rz), mean wave length of the shape (RSm) and surface texture parameter.

Patent Literature 1: Japanese Unexamined Patent Publication No. 2012-215486
Patent Literature 2: Japanese Unexamined Patent Publication No. 2003-500677

SUMMARY OF THE INVENTION

The inventions described in Patent Literatures 1 and 2, evaluate the surface property relative to the criteria of a plurality of measuring items by projecting a check pattern to a surface to be measured. However, these methods are not sufficient for an evaluating method, since it is not clear how the surface property thus evaluated is actually sensed by the human (observer) eyes (visual perception) and fingers (tactile perception).

The invention is directed to solve the above-described problem of the prior art, and the objective of the invention is to provide a method of evaluating a machined surface of a workpiece similar to that an observer actually evaluates with human sense, and a controlling apparatus and a machine tool using the evaluating method.

In order to achieve the above objective, the invention provides a method of evaluating a machined surface of a workpiece which uses evaluating criteria based on the characteristics of human sense.

Further, according to the invention, there is provided a control device for a feed axis of a machine tool, comprising a machined surface shape simulating section for simulating the machined surface of a workpiece by a calculation;

a contrast calculating section for calculating the maximum minimum luminance of reflecting light on the machined surface whereby the contrast is calculated based on the maximum minimum luminance; a spatial frequency calculating section for calculating spatial frequency of the machined surface;

judging section for determining whether or not the contrast of the machined surface can be visibly detected by the human visual perception, by using a contrast sensitivity function, based on the contrast and the spatial frequency; and a machining process modifying section for modifying a machining process, when the contrast of the processed surface is detectable by human visual perception, so that the contrast of the processed surface cannot be detected by human visual perception.

According to another feature of the invention, there is provided a control apparatus for a feed axis of a machine tool, comprising a machined surface shape simulating section for simulating a machined surface of a workpiece by a calculation; a vibration stimulus frequency calculating section for calculating vibration stimulus frequency transmitted to a finger of an observer when the observer fingers the machined surface simulated by the machined surface simulating section; a judging section for determining whether or not the amplitude of the vibratory stimulation, transmitted to the finger of the observer, can be detected by human tactile sense, relative to the frequency of the vibratory stimulation calculated by the vibration stimulus frequency calculating section, the amplitude of the vibratory stimulation being obtained based on the distance between peaks of cusps formed on the machined surface simulated by the machined surface simulating section, and the speed of the finger of the observer; and a process modifying section for modifying a machining process, when the amplitude of vibratory stimulation can be detected by human tactile sense, so that the amplitude of vibratory stimulation cannot be detected by human tactile sense.

According to another feature of the invention, there is provided a machine tool having at least three orthogonal feed axes of X-, Y- and Z-axes for relatively moving a tool to a workpiece, comprising a drive mechanism for driving the three feed axes; an NC device for controlling the drive mechanism; and an evaluating apparatus for simulating a machined surface formed on the workpiece;

wherein the evaluating apparatus comprising a machined surface shape simulating section for simulating the machined surface of a workpiece by a calculation; a contrast calculating section for calculating the maximum minimum luminance of reflecting light on the machined surface whereby the contrast is calculated based on the maximum minimum luminance; a spatial frequency calculating section for calculating spatial frequency of the machined surface; a judging section for determining whether or not the contrast of the machined surface can be visibly detected by the human visual perception, by using a contrast sensitivity function, based on the contrast and the spatial frequency; and a machining process modifying section for modifying a machining process, when the contrast of the processed surface is detectable by human visual perception, so that the contrast of the processed surface cannot be detected by human visual perception, whereby a tool path and a machining condition are sent to the NC device, based on the modified machining process.

According to another feature of the invention, there is provided a machine tool having at least three orthogonal feed axes of X-, Y- and Z-axes for relatively moving a tool to a workpiece, comprising a drive mechanism for driving the three feed axes; an NC device for controlling the drive mechanism; and an evaluating apparatus for simulating a machined surface formed on the workpiece;

wherein the evaluating apparatus comprising a machined surface shape simulating section for simulating a machined surface of a workpiece by a calculation; a vibration stimulus frequency calculating section for calculating vibration stimulus frequency transmitted to a finger of an observer when the observer fingers the machined surface simulated by the machined surface simulating section; a judging section for determining whether or not the amplitude of the vibratory stimulation, transmitted to the finger of the observer, can be detected by human tactile sense, relative to the frequency of the vibratory stimulation calculated by the vibration stimulus frequency calculating section, the amplitude of the vibratory stimulation being obtained based on the distance between peaks of cusps formed on the machined surface simulated by the machined surface simulating section, and the speed of the finger of the observer; and a process modifying section for modifying a machining process, when the amplitude of vibratory stimulation can be detected by human tactile sense, so that the amplitude of vibratory stimulation cannot be detected by human tactile sense, whereby a tool path and a machining condition are sent to the NC device, based on the modified machining process.

According the invention, the machining surface of a workpiece is evaluated based on criteria how it is actually sensed by human (observer) eyes (visual perception) and fingers (tactile perception), enabling objective evaluation based on the human sense, as well as production of workpieces, which are evaluated good by the human sense and accomplishes higher customer satisfaction. Further, there is provided a control device and a machine tool using the control device, which predicts the property of a machined surface by a simulation before the actual machining, automatically evaluates the property of the machined surface based on the criteria of human sense, and if it is predicted that there is a disturbance, which can be detected by the human sense, in the machined surface, then modifies the machining process so as to make the disturbance unable to be detected, enabling reduction in machining defect and increase in productivity.

DETAILED DESCRIPTION OF THE INVENTION

With reference to the attached drawings, a preferred embodiment will be described below.

Figure 1:
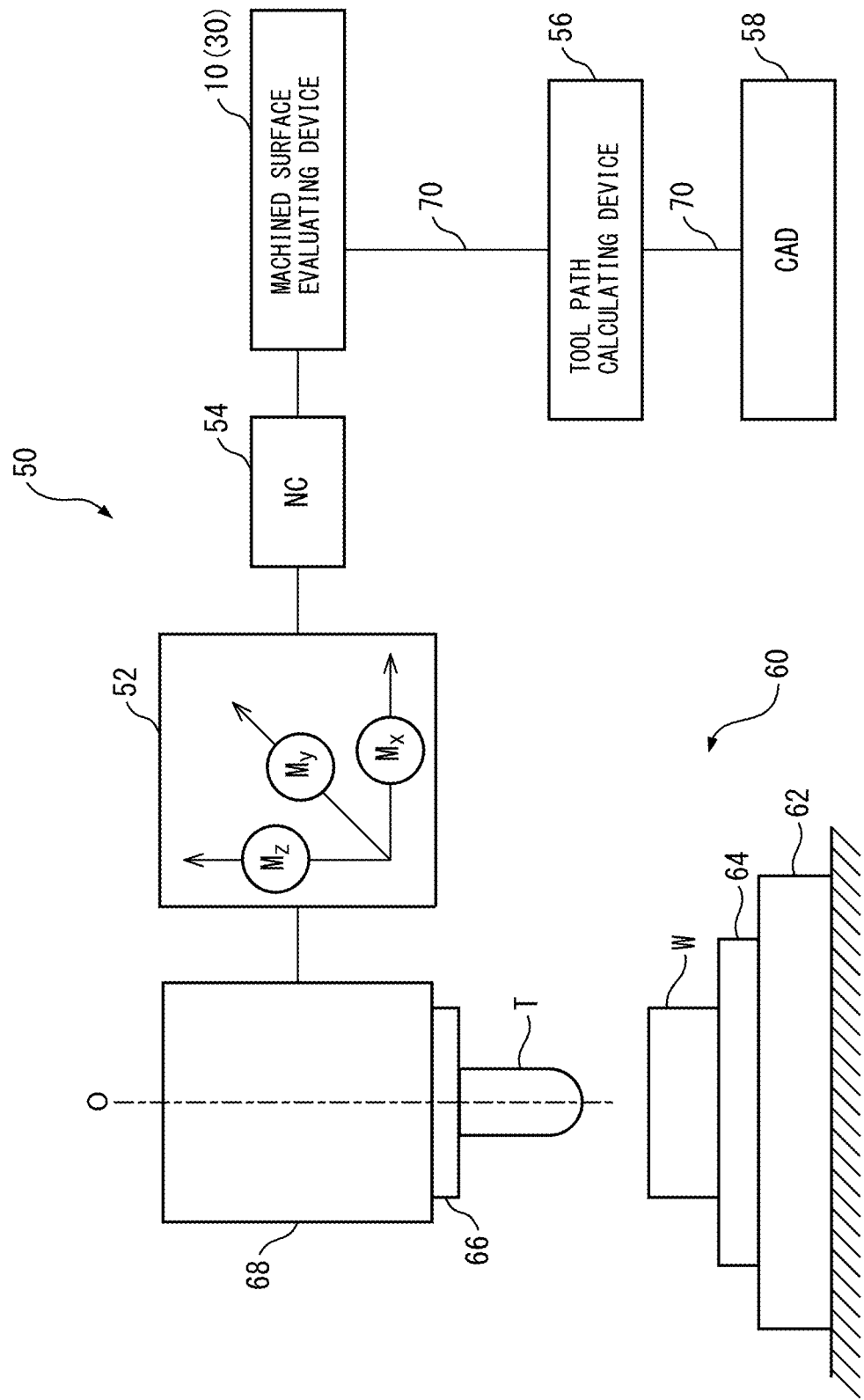
FIG. 1 is a schematic block diagram of a machine tool according to a preferred embodiment of the invention.

In FIG. 1, a machine tool 50 comprises a processing machine 60 and a machined surface evaluating apparatus 10 (30). The processing machine 60 comprises a bed 62 providing a base fixed to a flower of a factory, a table 64 mounted to a top of the bed 62 for attaching a workpiece W to a upper surface of the bed, a spindle head 68 for rotationally supporting a spindle 68 about a rotational axis O, the spindle 68 being adapted to receive a tool T facing the workpiece W attached to the table 64, a drive mechanism 52 for reciprocally driving the spindle head 68 in orthogonal three axes of X-, Y- and Z-axes, an NC device 54 for controlling servomotors of the drive mechanism 52, a tool path calculating device 56 for calculating and generating tool paths and sending data associated with the generated tool paths to the NC device 54, and the machined surface evaluating apparatus 10 (30), provided between the tool path calculating device 56 and the NC device 54, for correcting the tool path data sent to the NC device 54.

The drive mechanism 52 comprises for example X-, Y- and Z-axis ball screws (not shown), nuts (not shown) engaging the ball screws and X-, Y- and Z-axis drive motors Mx, My and Mz, each provided with a servomotor connected to one end of each X-, Y- and Z-axis ball screws, for rotationally driving the X-, Y- and Z-axis ball screws. Further, the machine tool 50 may include one or plurality of rotational feed axes such as an A-axis i.e., a rotational feed axis around the horizontal X-axis or a C-axis i.e., a rotational feed axis around the vertical Z-axis, in addition to the orthogonal three axes of X-, Y- and Z-axes. In such a case, the drive mechanism 52 includes servomotors for the feed axes i.e., A-axis and/or C-axis, in addition to the X-, Y- and Z-axis servomotors Mx, My and Mz.

The tool path calculating device 56 may be configured by for example a CAM device connected to a CAD device 58 through a computer network 70 such as a LAN so as to calculate tool paths based on shape data generated by CAD device 58 and to generate data associated with the tool paths for the machined surface evaluating apparatus 10 (30). The tool path calculating device 56 may be incorporated in a control program stored in a machine control device (not shown) of the processing machine 60 or the NC device 54.

Figure 2:
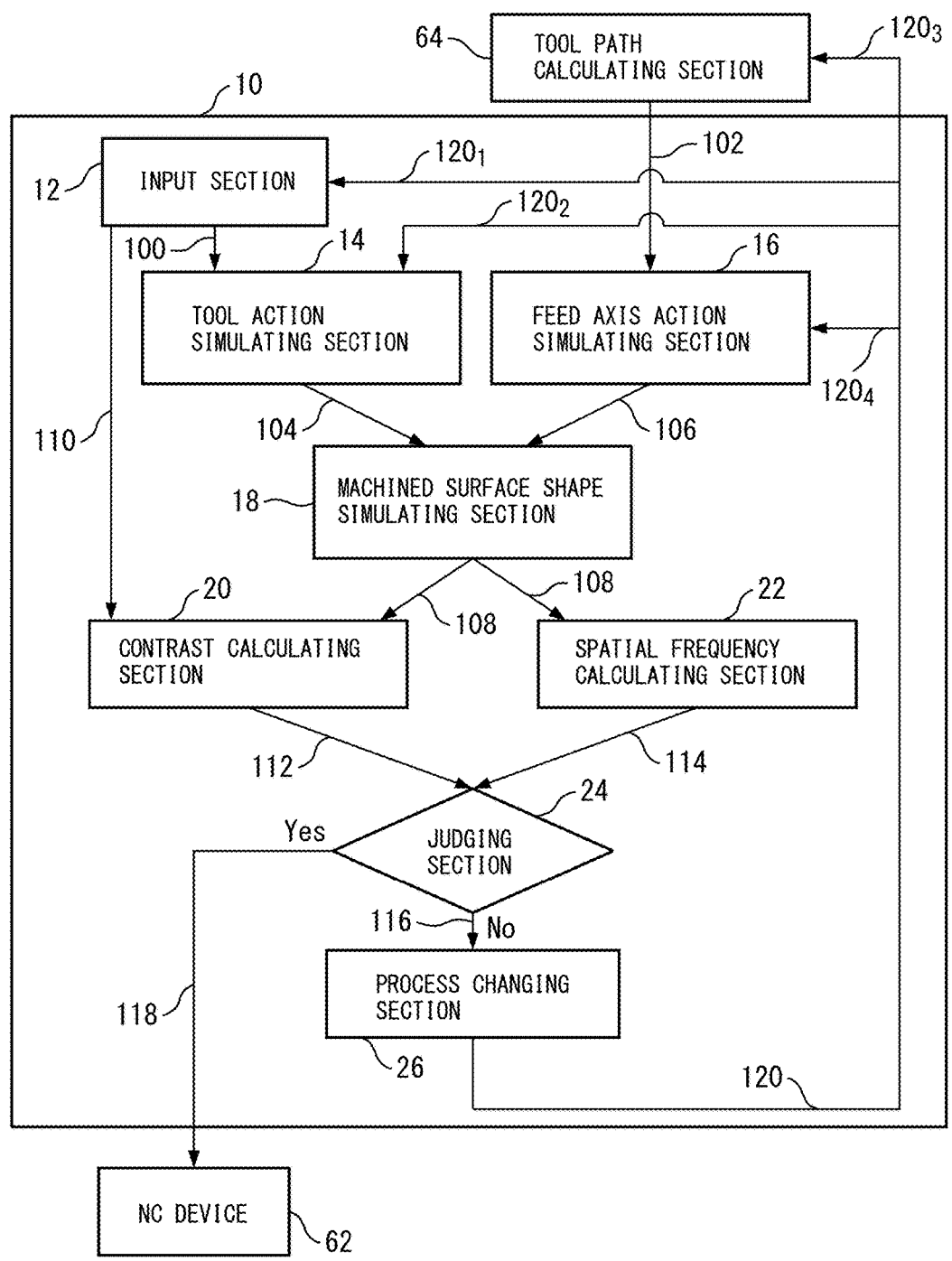
FIG. 2 is a block diagram of a machined surface evaluating apparatus according to a first embodiment of the invention.

With reference to FIG. 2, the machined surface evaluating apparatus 10 according to the first embodiment comprises, as its main elements, an input section 12, a tool action simulating section 14, a feed axis action simulating section 16, a machined surface shape simulating section 18, a contrast calculating section 20, a spatial frequency calculating section 22, a judging section 24 and a process modifying section 26.

Input into the tool action simulating section 14 and the feed axis action simulating section 16 at the input section 12 are data 100 associated with the machining condition, such as the material of the workpiece used in the machining process, the rotational speed of the spindle 66, the diameter, the length and the number of cutting edges of the tool T to be used, the cutting depth of the tool T into the workpiece W, the amount of the pick feed and the corrections of feeding speed of the respective feed axis. The input section 12 may be formed by, for example, a key board (not shown) or a touch panel of the NC device 54 or a machine controller (not shown) of the processing machine 60 or a database (not shown) stored in a server which is connected, along with the tool path calculating device 56, to a computer network.

The tool action simulating section 14 simulates, based on the machining condition which had been input through the input section 12, the action of the tool T such as the inclination of the tool T and/or the rotating movement of the ends of the cutting edges. The simulation results or Data 104 associated with the action of the tool T, are sent to the machined surface shape simulating section 18, as described below.

The feed axis action simulating section 16 simulates the actions of the three orthogonal linear feed axes of X-axis, Y-axis and Z-axis, and the rotational feed axes of the A-axis and C-axis, based on the tool path data 102 from the tool path calculating device 56 and the machining condition 100 input through the input section 12. The simulation results or data 100, associated with the actions of the three orthogonal linear feed axes of X-axis, Y-axis and Z-axis and the rotational feed axes of the A-axis and C-axis, are sent to the machined surface shape simulating section 18.

In the machined surface shape simulating section 18, the removal of chips from the workpiece W by the machining process is simulated, based on the data 104 associated with the action of the tool T and the data 106 associated with the actions of the feed axes, whereby the shape of the machined surface formed in the workpiece W, in particular the height of cusps, the interval between adjacent cusps, the inclination of the sides of cusps, etc. The calculation results or data 108 associated with the shape of the machined surface of the workpiece W are sent to the contrast calculating section 20 and the spatial frequency calculating section 22.

Input into the contrast calculating section 20 through input section 12 are data 110 including the data associated with the material of the workpiece W, the data associated with the light source, such as the intensity of illumination, the wave length and the coordinate of the light source, and the data associated with the observer, such as the angle of the line of sight when a possible observer takes a look at the workpiece. In case of the workpiece W is a metallic mold used in an injection molding machine, it is preferable to input the data associated with the plastic material molded in the metallic mold, instead of the data associated with the material of the workpiece W. The contrast calculating section 20 calculates the maximum luminance Lmax and the minimum luminance Lmin of the light reflected on the workpiece W, based on the data 108 associated with the shape of the machined surface of the workpiece W from the machined surface shape simulating section 18 and the data 110 input through the input section 12, whereby the contrast of the surface of the workpiece W is calculated. The calculation results or the contrast m is sent to the judging section 24.

Figure 3:
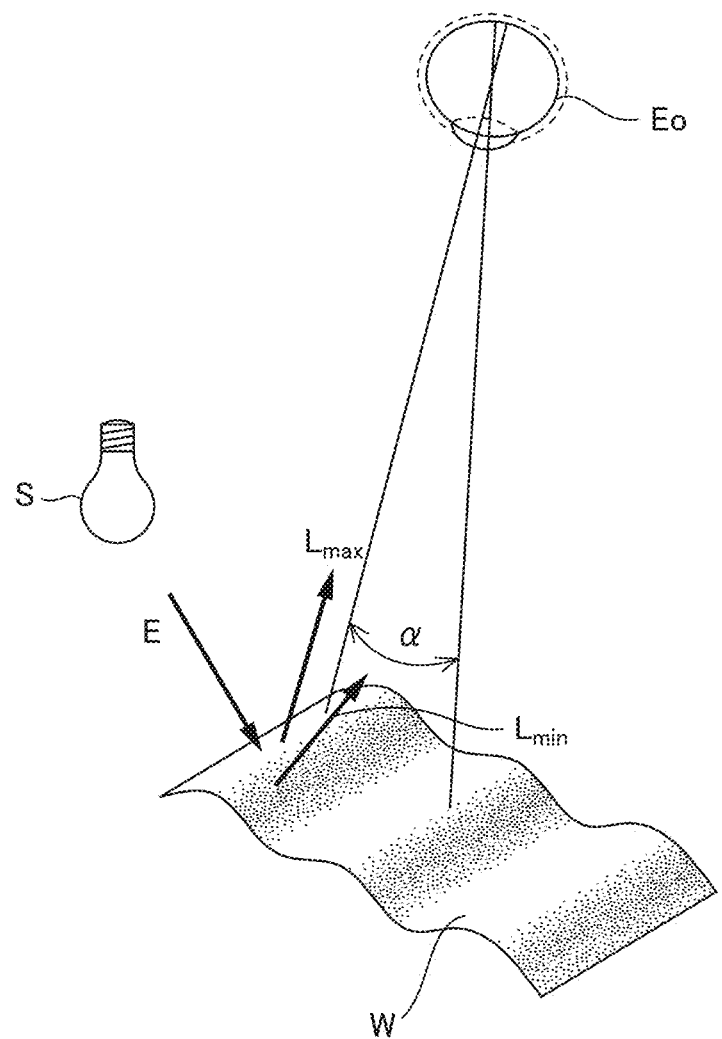
FIG. 3 is a schematic illustration for explaining contrast.

With reference to FIG. 3, the contrast m is obtained by the following formulation.

$$m = (L\text{max} - L\text{min})/(L\text{max} + L\text{min})$$

where:
Lmax: Maximum Luminance (cd/m2)
Lmin: Minimum Luminance (cd/m2)

Further, the luminance is obtained by the following formulation.

$$L = \beta(\theta i, \theta r) \cdot (\rho/\pi) \cdot E$$

where:
β: Luminance Ratio
θi: Angle of Incidence (deg)
θr: Angle of Reflection (deg)
ρ: Reflectance
E: Intensity of Illumination of the Incident Light from the Light Source S (1×)

Figure 4:
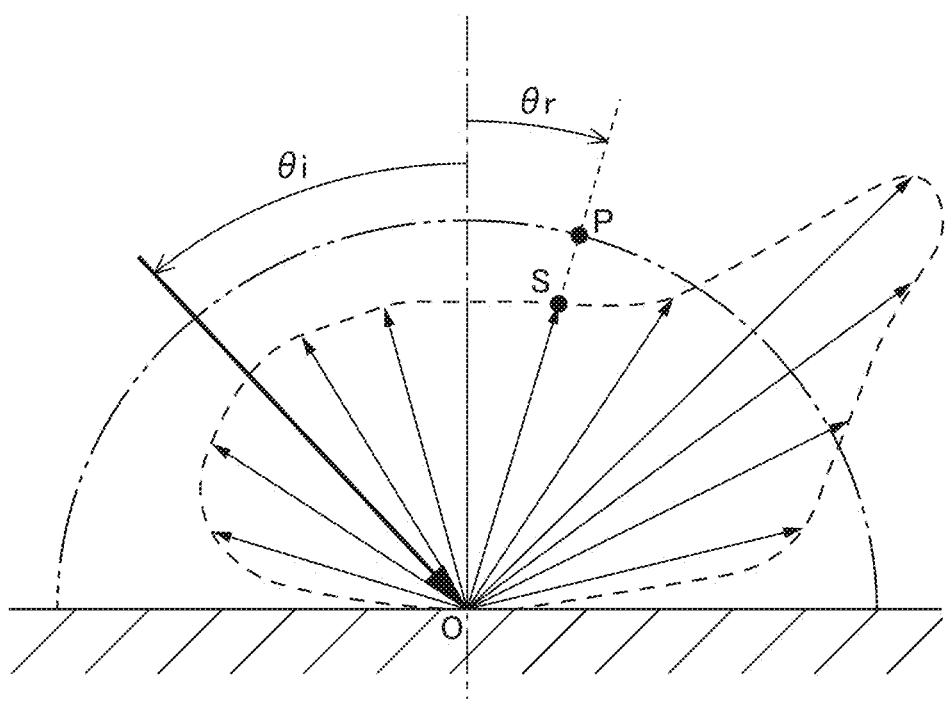
FIG. 4 is a schematic illustration for explaining luminance ratio.

With reference to FIG. 4, the luminance ratio β is the ratio of the luminance L(θr) on a sample surface in the diction of the angle of reflection (θr) among the diffuse reflection, shown by the broken line, on an actual reflecting surface relative to the luminance Lpd (shown by lines OP), which is constant in the all directions, as shown by two-dot chain line, on a perfect diffusively reflecting surface. On a perfect diffusively reflecting surface, the luminance is constant in all directions, while the luminance varies depending on the reflection angle θr on an actual surface. An example of a method for obtaining the luminance ratio β may include previously measuring the luminance of the reflected light, with respect to a variety of material, by a measuring device, such as a luminance meter, at a plurality of reflection angles θr, with the incident angle θr being changed, whereby the luminance ratios β are stored in the contrast calculating section 20 in the form of a table (database) or approximation formulas, associated with the incident angle θi and the reflection angle θr, as parameters, with regard to a variety of material for the workpiece W.

The contrast calculating section 20 can lock for the contrast m by calculating the incident angle θi to the machined surface and the reflection angle θr on the machined surface, based on the data input through the input section 12, in particular the material of the workpiece W, the distance between the workpiece W and the eyes of the observer, and the data 108 associated with the machined surface from the machined surface simulating section 18, obtaining the luminance ratio β(θi, θr) by referring to the table (database) in association with the parameters, i.e., the material of the workpiece W, the incident angle θi and the reflection angle θr, and obtaining the maximum luminance Lmax and the minimum luminance Lmin based on the luminance ratio β(θi, θr).

The spatial frequency calculating section 22 calculates the spatial frequency ω based on the data 108, associated with the shape of the machined surface, from the machined surface shape simulating section 18. With reference to FIG. 3, the spatial frequency ω is defined by the reciprocal of the angle of view α, which is the angle between the adjacent cusps projected to the eye E0 of the observer, or the number of the cusps per the angle of view α=1 degree. The calculation results of the spatial frequency ω are sent to the judging section 24. The maximum luminance Lmax and the minimum luminance Lmin are determined by securing the line of sight and the machined surface, locking for the angle of view α at which the luminance is maximum with the angle of view getting widen, and setting the luminance as the maximum luminance Lmax and the luminance, at the side opposite to the angle of view α, as the minimum luminance Lmin.

Figure 5:
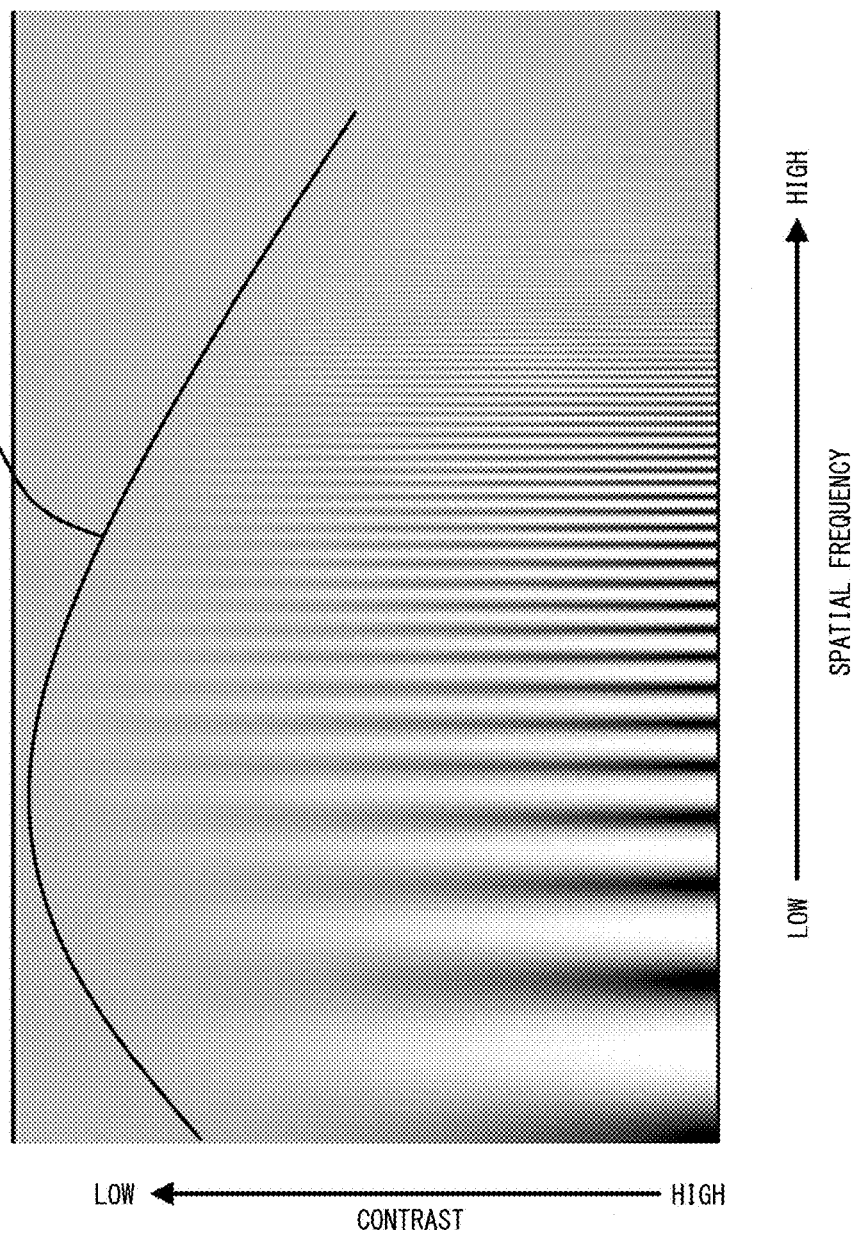
FIG. 5 is a chart for explaining a contrast sensitivity function.

The judging section 24 determines, based on the contrast m from the contrast calculating section 20 and the spatial frequency ω from the spatial frequency calculating section 22, whether or not human eyes can recognize the cusps on the surface of the workpiece W, machined by the machining process, as strips by using a contrast sensitivity function. With reference to FIG. 5, the human visual perception cannot in general discriminate the difference in luminance when the contrast is lower. The minimum contrast, at which the difference in contrast can be discriminate, is referred to as contrast threshold, and the reciprocal of contrast threshold is referred to as contrast sensitivity. Contrast sensitivity varies depending on spatial frequency, and the changes in contrast sensitivity relative to spatial frequency is generally referred to as contrast sensitivity curve or contrast sensitivity function Fcs. It is generally known that contrast sensitivity function Fcs has a peak at a spatial frequency of 4 cycle/degree, and that when the spatial frequency is higher or lower than it, contrast sensitivity is reduced.

In this embodiment, the judging section 24 determines, based on the contrast m from the contrast calculating section 20 and the spatial frequency ω from the spatial calculating section 22, whether or not the contrast of the stripes of the cusps on the machined surface of the workpiece W formed by the machining process is at the higher side (the strips are visible) or the lower side (the strips are invisible) relative to the contrast sensitivity function Fcs. While contrast sensitivity function Fcs varies from person to person, a preliminary experiment may be carried out whereby a suitable contrast sensitivity function Fcs is stored in the judging section 24. Alternatively, a plurality of sensitivity functions Fcs may be stored in the judging section 24, allowing a user to choose one advantageously.

When the judging section 24 judges (Yes) that the contrast m from the contrast calculating section 20 and the spatial frequency ω from the spatial frequency calculating section 22 fall in the upper region (the strips are invisible) higher than the contrast sensitivity function Fcs in FIG. 5, the machined surface evaluating apparatus 10 sends the machining condition input through the input section 12 and the data 118 associated with the tool path generated by the tool path calculating device 64 to the NC device 62.

When the judging section 24 judges (No) that the contrast m from the contrast calculating section 20 and the spatial frequency ω from the spatial frequency calculating section 22 fall in the lower region (the strips are visible) lower than the contrast sensitivity function Fcs in FIG. 5, the machined surface evaluating apparatus 10 commands at least one of the input section 12 (command $120_1$), the tool action simulating section 14 (command $120_2$), the tool path calculating device 64 (command $120_3$) and the feed axis action simulating section 16 (command $120_4$) so as to modify the machining process. The process modification may include changing in the rigidity of the bearings for supporting the spindle 66 for rotation and the tool path generated by the tool path calculating device 56, as well as changing in the machining condition, such as the rotational speed of the spindle 66, the feeding speed of the respective feed axes, the diameter, the length and the number of the cutting edges of the tool T to be used, the cutting depth of the tool T into the workpiece W, the amount of pick feed and/or the correction value for the feeding speed of the respective feed axis.

Figure 6:
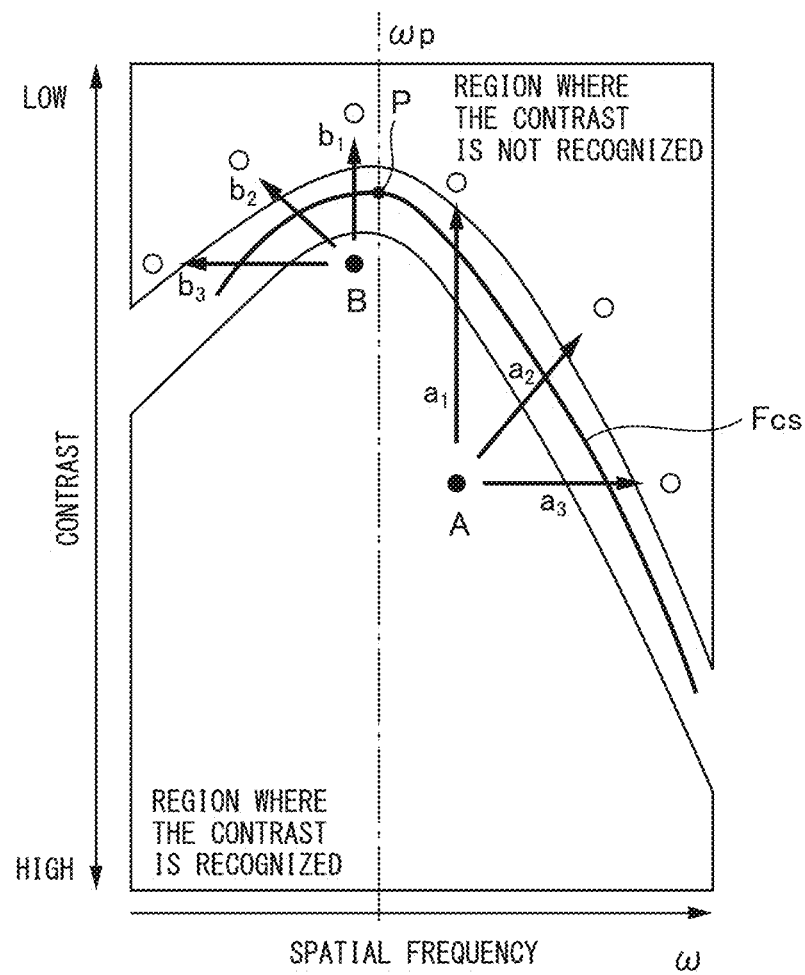
FIG. 6 is a schematic illustration for explaining a method for modifying the process.

With reference to FIG. 6, if the spatial frequency ω from the spatial frequency calculating section 22 is larger than the spatial frequency ωp, providing the peak P of the contrast sensitivity function Fcs, as shown by point A in FIG. 6, then the process modifying section 26 modifies the machining process so as to reducing the contrast m (a1) or so as to reduce the contrast m and increase the spatial frequency ω (a2). On the other hand, if the spatial frequency ω from the spatial frequency calculating section 22 is smaller than the spatial frequency ωp, providing the peak P of the contrast sensitivity function Fcs, as shown by point B in FIG. 6, then the process modifying section 26 modifies the machining process so as to reducing the contrast m (b1) or so as to reduce the contrast m and the spatial frequency ω (b2).

Figure 7:
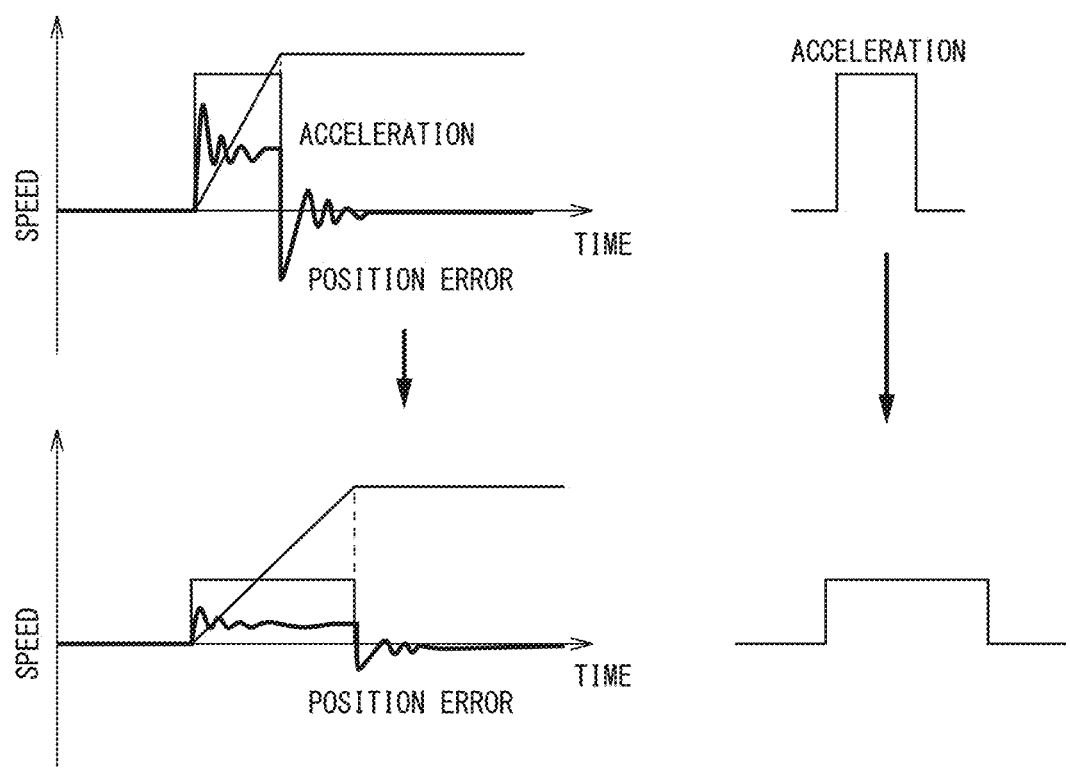
FIG. 7 is a chart showing an example of the process modification.

The process modifications a1, b1 for reducing the contrast m can be carried out by, for example, outputting the command $120_1$, for reducing the diameter of the tool T to be used, to the input section 12. Alternatively, when the bearings for rotationally supporting the spindle in the spindle head 68 include a magnetic bearing using magnetic force, then the command $120_2$, for reducing the magnetic force of the magnetic bearing, may be sent to the tool action simulating section in order to reduce the stiffness of the bearing so that the size of the entire cusps increases, whereby the local cusps become less noticeable and the contrast m is reduced. Further, the command $120_4$, for reducing the feeding speed of the feed axes, may be to the feed axis simulating section 16, as shown in FIG. 7, in order to reduce the height of the cusps, which can be generated based on the positions errors during the acceleration and deceleration of the feed axes, whereby the contrast m is reduced.

Figure 8:
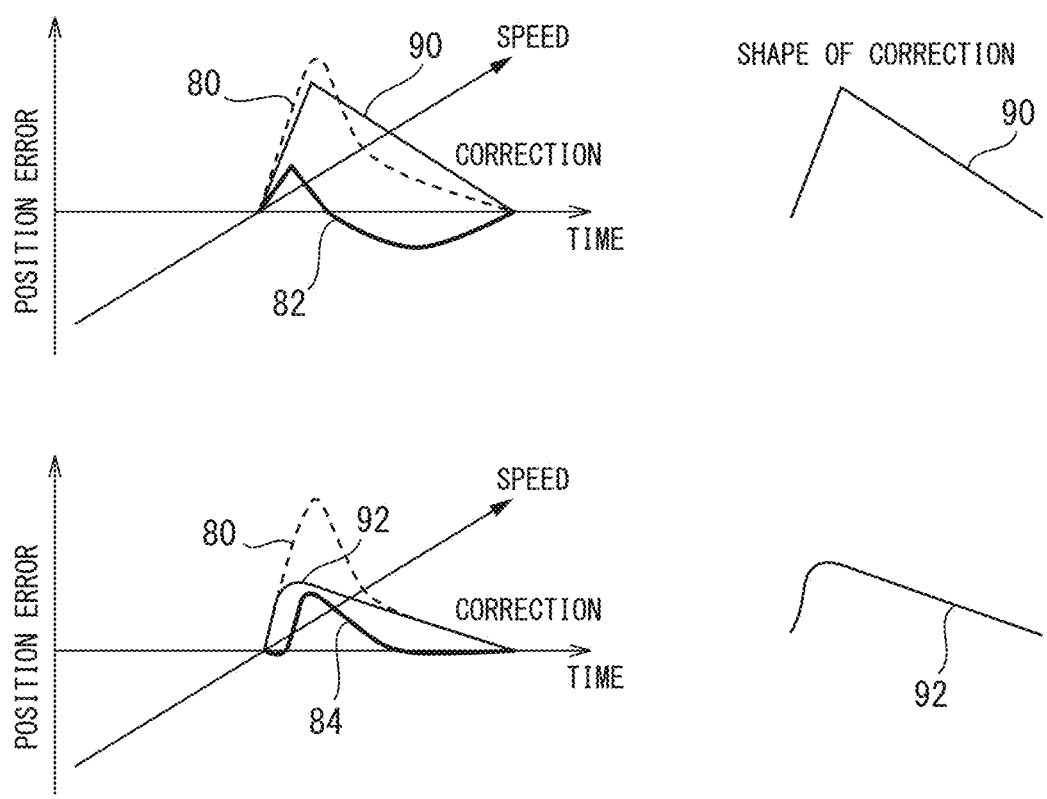
FIG. 8 is a chart showing another example of the process modification.

Furthermore, the command $120_4$, for modifying the correction filter sent to the servomotors when the rotation of the feed axes is reversed, may be sent to the feed axis simulating section 16. For example, by modifying the correction filter in to a small and smooth shape, as shown in FIG. 8, the shape of the machined surface of the workpiece W is smooth, while the absolute value of position error associated with quadrant change, whereby the contrast m is reduced and the spatial frequency ω is changed (directions a2 and b2).

Accordingly, in this embodiment, until stripes on the machined surface of the workpiece W cannot be visibly detected by an observer or the judgment by the judging section 24 is Yes, the modification of the machining process is repeated. As described above, in this embodiment, it is estimated, using the contrast sensitivity function Fcs, whether or not strips can be visibly detected by an observer, based on the contrast m of the strips generated by the cusps formed on the machined surface of the workpiece and the spatial frequency ω, and the machining process is modified until the strips on the machined surface cannot be visibly detected by an observer.

Figure 9:
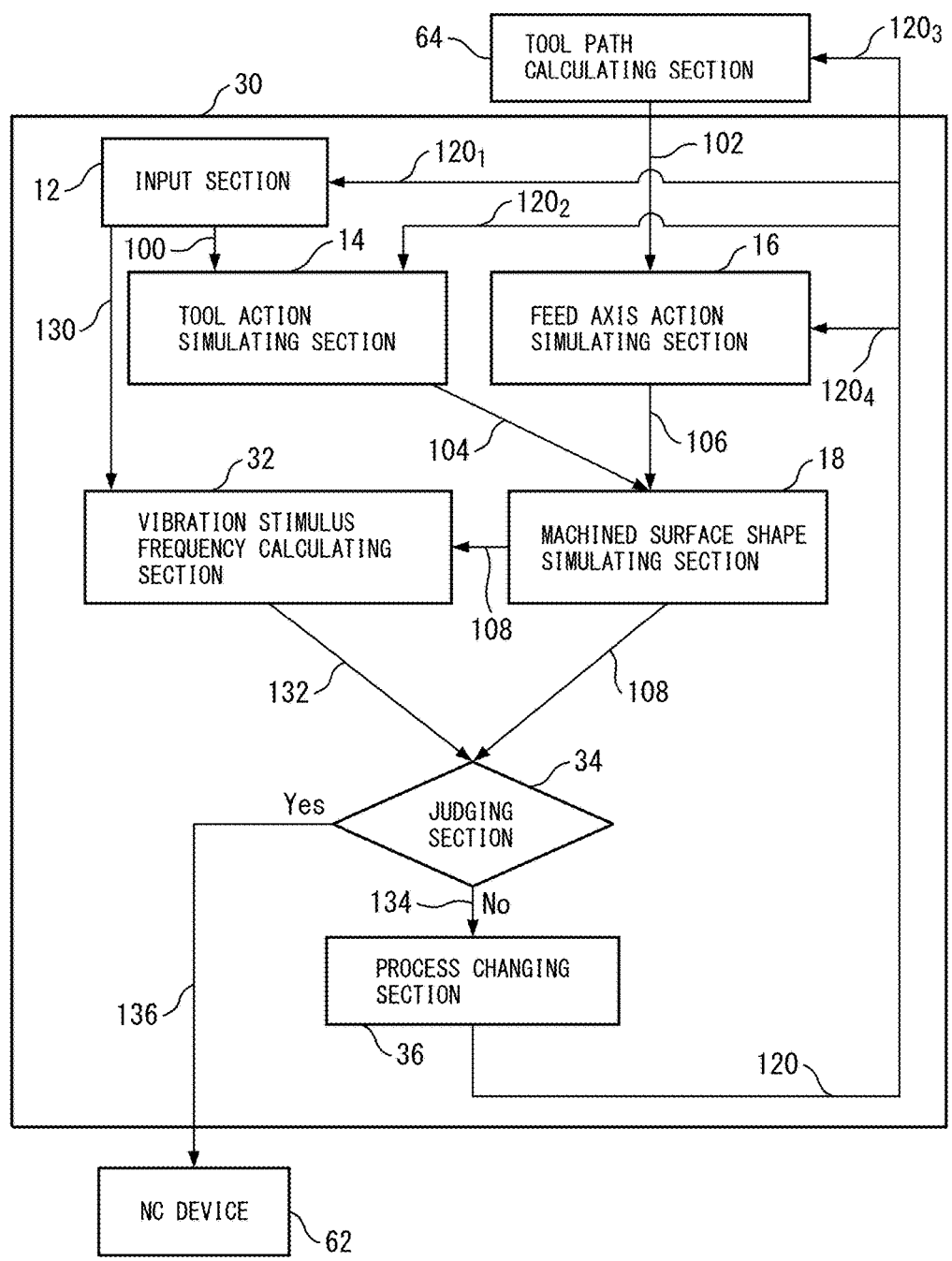
FIG. 9 is a block diagram of a machined surface evaluating apparatus according to a second embodiment of the invention.

With reference to FIG. 9, a second embodiment of the present invention will be described. In the first embodiment, the human visual perception, in particular, the contrast sensitivity is used as a human-sense based evaluation criteria for a machined surface. In the second embodiment, the human tactile perception, in particular the characteristics of frequency threshold of the human tactile perception is used as the evaluation criteria. In FIG. 9, the elements similar to those in FIG. 2 are indicated by the same references.

With reference to FIG. 9, a machined surface evaluating apparatus 30 according to the second embodiment includes a vibration stimulus frequency calculating section 32, instead of the contrast calculating section 20 and the spatial frequency calculating section 22 of the machined surface evaluating apparatus 10 of the first embodiment. In the second embodiment, the speed 130 of finger(s) of an observer sliding along the machined surface of the workpiece W (the relative speed to the machined surface) and the data 108 associated with the machined surface, in particular the distance between the adjacent cusps are input into the vibration stimulus frequency calculating section 32 through the input section 12 and the machined surface shape calculating section 18, respectively.

The vibration stimulus frequency calculating section 32 calculates the vibration stimulus frequency, which is transmitted to the finger(s) of the observer, and sent the data associated with the calculation results or the vibration stimulus frequency to the judging section 34. Further, the data 108 associated with the machined surface, in particular the distance between the adjacent cusps are sent to the judging section 34 from the machined surface shape calculating section 32.

Figure 10:
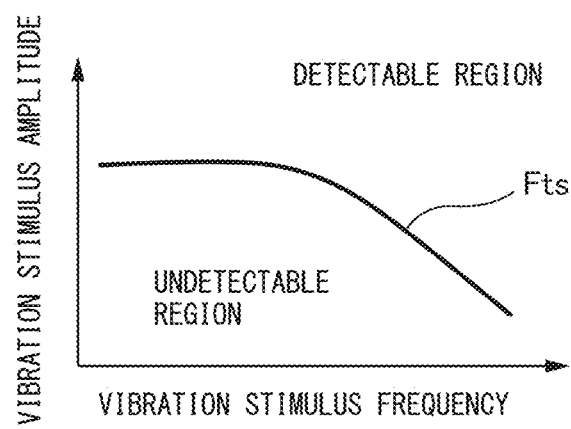
FIG. 10 is a chart for explaining characteristics of frequency threshold of human sense.

With reference to FIG. 10, it is generally known that human tactile perception has characteristics that at a higher vibration stimulus frequency, small amplitude of vibratory stimulation cannot be detected (the characteristics of frequency threshold of the human tactile perception). In this embodiment, the judging section 34 determines, based on the vibration stimulus frequency obtained from the vibration stimulus frequency calculating section 34 and the amplitude of the vibratory stimulation transmitted to the finger of an observer, which is calculated based on the distance between the peaks of the adjacent cusps and the speed of the finger of the observer, whether or not the observer can recognize the cusps on the surface of the workpiece W, machined by the machining process, by touching them with the finger.

Although the curve or function Fts, representing the frequency threshold characteristics of human tactile perception, shown in FIG. 10, differs from person to person, a suitable frequency threshold function Fts can be previously stored based on an experiment. Alternatively, a plurality of frequency threshold functions Fts may be stored in the judging section 24 so as to allow a user to choose one.

As described above, in this embodiment, the judging section 34 determines, based on vibration stimulus frequency and the distance between the peaks of adjacent cusps, whether or not the cusps on the machined surface of the workpiece W formed by the machining process falls in the higher side (the cusps are sensible) or the lower side (the cusps are sensible) relative to the frequency threshold function Fts of the human tactile perception, and repeats the modification of the machining process, until the cusps on the machined surface of the workpiece W cannot be detected by the tactile perception of an observer or the judgment by the judging section 24 is Yes.

REFERENCE SIGNS LIST

10 Machined Surface Evaluating Apparatus
12 Input Section
14 Tool Action Simulating Section
16 Feed Axis Action Simulating Section
18 Machined Surface Shape Simulating Section
20 Contrast Calculating Section
22 Spatial Frequency Calculating Section
24 Judging Section
26 Process Modifying Section
30 Machined Surface Evaluating Apparatus
32 Vibratory Stimulus Frequency Calculating Section
34 Judging Section
50 Machine Tool
56 Tool Path Calculating Section
62 Bed
64 Table

The invention claimed is:

1. A method comprising the steps of:
obtaining a shape of machined surface of a workpiece and shapes of cusps formed in the machined surface by simulation calculation based on a given set of machining conditions of the workpiece;
calculating luminance of reflecting light on the machined surface based on the obtained shape of the machined surface and the obtained shapes of the cusps;
calculating a contrast based on the luminance of reflecting light;
calculating a spatial frequency of the machined surface based on intervals between the cusps in the machined surface;
determining a position of the machined surface in a contrast sensitivity function diagram having a contrast axis and a spatial frequency axis and presenting a contrast sensitivity curve that separates a first region of the diagram from a second region of the diagram; and
not changing the machining conditions when the position of the machined surface in the diagram falls in the first region, and changing the machining conditions so as to reduce visibility of the cusps on the machined surface when the position of the machined surface in the diagram falls in the second region.

* * * * *